United States Patent [19]

Clubley et al.

[11] Patent Number: 4,719,036
[45] Date of Patent: Jan. 12, 1988

[54] COMPOSITIONS CONTAINING HETEROCYCLIC CORROSION INHIBITORS

[75] Inventors: Brian G. Clubley, Wilmslow; Emyr Phillips, Sale, both of England

[73] Assignee: Ciba-Geigy Corporation, Ardsley, N.Y.

[21] Appl. No.: 731,816

[22] Filed: May 8, 1985

[30] Foreign Application Priority Data

May 11, 1984 [GB] United Kingdom ............... 8412064

[51] Int. Cl.$^4$ ........................................... C09K 15/30
[52] U.S. Cl. .................................. 252/391; 252/49.3; 252/49.5; 252/75; 252/78.1; 106/14.23; 106/14.35; 524/83; 548/165; 548/170; 548/171; 548/173
[58] Field of Search ............... 252/391, 75, 78.1, 49.5, 252/49.3; 548/165, 170, 171, 173; 524/83; 106/14.23, 14.35

[56] References Cited

U.S. PATENT DOCUMENTS

| | | | |
|---|---|---|---|
| 2,136,332 | 11/1938 | Clifford | 548/171 X |
| 2,136,949 | 11/1938 | Orthner et al. | 548/171 X |
| 2,158,021 | 5/1939 | Lichty | 525/332.7 |
| 2,413,917 | 1/1947 | Harman | 548/165 X |
| 2,642,396 | 6/1953 | Roddy, Jr. | 252/47 |
| 2,725,364 | 11/1955 | Pazzi | 524/83 |
| 2,725,382 | 11/1955 | Harmon | 548/170 |
| 2,939,789 | 6/1960 | Dersch et al. | 548/170 |
| 3,049,509 | 8/1962 | Hardy et al. | 524/83 |
| 3,379,875 | 4/1968 | Holoch | 524/83 |
| 4,000,079 | 12/1976 | Rasp et al. | 252/391 X |
| 4,011,194 | 3/1977 | Sandler | 524/83 |
| 4,235,838 | 11/1980 | Redmore et al. | 252/391 |
| 4,294,839 | 10/1981 | Doll et al. | 548/170 X |
| 4,329,381 | 5/1982 | Eschwey et al. | |
| 4,448,399 | 5/1984 | D'Amico | 548/165 |
| 4,554,355 | 11/1985 | Musser | 548/171 X |
| 4,594,425 | 6/1986 | Musser et al. | 548/171 X |

FOREIGN PATENT DOCUMENTS

| | | | |
|---|---|---|---|
| 67685 | 12/1982 | European Pat. Off. | |
| 2301461 | 7/1973 | Fed. Rep. of Germany | 524/83 |
| 73185 | 5/1982 | Japan | 252/391 |
| 448414 | 5/1935 | United Kingdom | |
| 564412 | 9/1944 | United Kingdom | |
| 2019392 | 10/1979 | United Kingdom | |

OTHER PUBLICATIONS

Edwards et al., "Nonmercurial Preservatives, Their Effectiveness and Relationship to Raw Materials in Latex Paints", *J. Paint Technol*, vol. 46 (509)(Feb. 1974), pp. 37–45.
Chemical Abstract No. 101:145,862 (1984), p. 235, "Mildewcide Testing . . . ".
Chemical Abstract No. 93:199038 (1980), p. 191, "Study of Biocidal and . . . ".
Chemical Abstract No. 81:137,665 (1974), p. 80, "Antifouling Marine Paint".
O. A. Orio et al., C.A. 69, 96541a (1968).
J. Herdan et al., Rev. Roum. Chim. 28, 757 (1983).
G. F. Galenko et al., C.A. 83, 79146x (1975).
H. Wienand et al., Farbe & Lack, 88, 183 (1982).

*Primary Examiner*—Matthew A. Thexton
*Attorney, Agent, or Firm*—Luther A. R. Hall

[57] ABSTRACT

New anticorrosive compositions comprise:
(A) an applicational medium selected from (a) surface coatings and (b) wholly or partly aqueous non-coating media,
(B) as corrosion inhibitor, an amide, imide or nitrile of an aliphatic- or cycloaliphatic mono-, di-, tri- or tetracarboxylic acid which is substituted in the aliphatic- or cycloaliphatic residue by one or more groups having the formula:

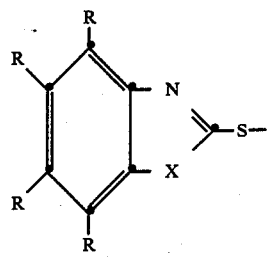

I in which X is oxygen, sulphur or NH; and each R, independently, is hydrogen, alkyl, haloalkyl, alkoxy, alkylthio, alkylsulphonyl, cycloalkyl, phenyl, alkylphenyl, phenylalkyl, halogen, cyano, nitro, hydroxy, —COOH, —COOalkyl or a primary-, secondary- or tertiary amino- or carbamoyl group; or a non-toxic base addition salts of those components (B) which contain free carboxyl groups.

26 Claims, No Drawings

COMPOSITIONS CONTAINING HETEROCYCLIC CORROSION INHIBITORS

The present invention relates to new compositions comprising as corrosion inhibitor, amides, imides or nitriles of carboxylic acids which contain a heterocyclic residue; and to certain new compounds.

Effecctive corrosion inhibition is one of the most important requirements for organic coatings applied onto metal substrates. Many proposals for improving the corrosion inhibition of paints can be found in the literature e.g. in H. Kittel, Lehrbuch der Lacke und Beschichtungen, Band V, 1977. Thus the barrier function of the coatings may be improved, thereby preventing corrosive agents such as oxygen, water and ions from reaching the metal surface where corrosion starts. Yet another possibility, most commonly practised today, is the addition of anticorrosive pigments which chemically, or electrochemically, interfere in the corrosion process by forming insoluble deposits with corrosion products e.g. alkali or metal ions, or by passivating (polarising) the metal surface. Amongst the most active anticorrosive pigments are metallic chromates and lead compounds (oxides etc.). Metallic chromates have been widely used as anticorrosive pigments in paints because of their activity in both the anodic and cathodic areas of protection. There is now some concern, however, about the environmental risks involved in the use of chromates because of their potential carcinogenic activity. Similarly, the chronic toxicity of lead compounds is causing great concern in the paint industry.

Metal salts or organic compounds have also been proposed as corrosion inhibitors for use in coatings. In European Patent Specification No. 3817, for example, the use is described of zinc- or lead salts of hydroxyl- or mercapto compounds of 5- or 6-membered heterocyclic compounds which contain the characteristic group —N=C(OH)— or —N=C(SH)—. Typical examples are the zinc- and lead salts of 2-mercaptobenzothiazole. These known inhibitors, therefore, optionally contain toxic lead salts.

In the surface coatings field it has previously been doubted (Funke, Farbe und Lack, 87, (1981), 787) that the addition of organic corrosion inhibitors alone could provide sufficient corrosion inhibition in practice.

We have now found certain heterocyclic carboxylic acid amides, imides and nitriles (and their non-toxic salts), which are useful as corrosion inhibitors in surface coatings and, which allow the formulation of highly effective chromate- and lead-free anti-corrosive paints. The new corrosion inhibitors are not pigments and their use in surface coatings thus leaves the formulator a free choice of pigment or filler.

It is therefore surprising, that the organic amide, imide and nitrile corrosion inhibitors used according to the invention exhibit in surface coatings a corrosion-inhibiting effect which is comparable to, or even better than that of chromate- or lead pigments. Moreover, these organic corrosion inhibitors exhibit excellent corrosion inhibition in wholly or partly aqueous media.

According to the present invention there is provided a composition comprising (A) an applicational medium selected from (a) surface coatings and (b) wholly or partly aqueous non-coating media; and (B) as corrosion inhibitor, an effective corrosion-inhibiting amount of one or more aliphatic- or cycloaliphatic mono-, di-, tri- or tetra-carboxylic acid amides or imides (as hereinafter defined) or nitriles which are substituted in the aliphatic- or cycloaliphatic residue by one or more groups, preferably only one group having the formula:

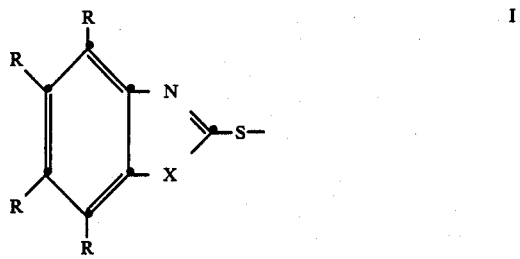

I in which X is oxygen, sulphur or NH; and each R, independently, is hydrogen, alkyl, haloalkyl, alkoxy, alkylthio, alkylsulphonyl, cycloalkyl, phenyl, alkylphenyl, phenylalkyl, halogen, cyano, nitro, hydroxy, —COOH, —COOalkyl or a primary-, secondary- or tertiary amino- or carbamoyl group; or a non-toxic base addition salt of those components (B) which contain free carboxyl groups.

By "amides" of aliphatic or cycloaliphatic mono-, di-, tri- or tetra-carboxylic acids, we mean the full or partial amides containing 1 to 4 groups —$CONZ_1Z_2$ or —COOH in which $Z_1$ and $Z_2$, independently, are H; $C_1$–$C_{18}$ alkyl optionally interrupted by one or more O or S atoms or by one or more $NR^o$ groups (in which $R^o$ is $C_1$–$C_{18}$ alkyl, $C_3$–$C_{12}$ cycloalkyl, phenyl, naphthyl, $C_7$–$C_9$ phenylalkyl, or $C_7$–$C_{18}$ alkylphenyl) or optionally substituted by SH, $NH_2$, COOH, $COOR^o$ (wherein $R^o$ has its previous significance), $CONH_2$, CN or halogen (preferably F, Cl or Br); $C_2$–$C_{10}$ hydroxyalkyl optionally interrupted by one or more $NR^o$ groups (wherein $R^o$ has its previous significance) or O atoms; $C_3$–$C_{18}$ alkenyl; $C_3$–$C_{12}$ cycloalkyl optionally substituted by $C_1$–$C_4$ alkyl, OH, SH, COOH, $COOR^o$ (wherein $R^o$ has its previous significance), $CONH_2$, CN or halogen (preferably F, Cl or Br); $C_7$–$C_9$ phenylalkyl; $C_7$–$C_{18}$ alkylphenyl; or $C_6$–$C_{10}$ aryl which may be optionally substituted by $C_1$–$C_{12}$ alkoxy, $C_1$–$C_{12}$ alkylthio, halogen (preferably F, Cl or Br) or nitro; or $Z_1$ and $Z_2$ together form an optionally branched $C_3$–$C_7$ alkylene group optionally interrupted by O, S or $NR^o$ (wherein $R^o$ has its previous significance) provided that at least one group —$CONZ_1Z_2$ is present. If the amide contains more than one group —$CONZ_1Z_2$ the respective —$CONZ_1Z_2$ may be the same or different.

By "imides" of aliphatic or cycloaliphatic monocarboxylic acids we mean symmetrical or unsymmetrical imides optionally substituted on the imide nitrogen by a residue $Z_1$, in which $Z_1$ has its previous significance. viz. a group —CO.N($Z_1$).CO— derived from 2 moles of the monocarboxylic acid and one mole of amine.

By "imides" of aliphatic- or cycloaliphatic di-, tri- or tetra-carboxylic acids we mean cyclic imides containing, the grouping III or IIIa on IVa

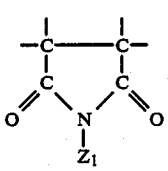

III

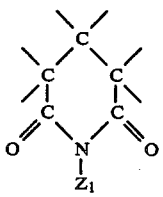

wherein $Z_1$ has its previous significance.

Depending on whether X is oxygen, sulphur on NH, the amides, imides and nitriles used in the compositions of the invention are benzoxazoles, benzothiazoles or benzimidazoles; benzothiazole amides, imides and nitriles are preferred, especially amides and, most especially, half-amides.

R is alkyl, alkoxy, alkylthio or alkylsulphonyl preferably contains 1-12 C-atoms, especially 1-6 C-atoms. Examples include methyl, ethyl, n-propyl, isopropyl, n-butyl, isobutyl, tert.-butyl, n-pentyl, n-hexyl, n-octyl, 1,1,3,3-tetramethylbutyl, n-nonyl, n-decyl, n-undecyl, n-dodecyl and t-dodecyl and the corresponding alkoxy-, alkylthio- and alkylsulphenyl radicals.

R as cycloalkyl contains 3-12 C-atoms preferably 5-8 C-atoms e.g. cyclopropyl, cyclobutyl, cyclopentyl, cyclohexyl, cyclooctyl or cyclododecyl.

R as haloalkyl preferably contains 1-4 C-atoms and 1-3 F- or Cl— atoms e.g. chloromethyl, fluoromethyl, di- and tri-fluoromethyl or 2-chloroethyl.

R as alkylphenyl preferably contains 7-18 C-atoms and is e.g. tolyl, xylyl, 4-isopropylphenyl, 4-tert.-butyl-phenyl, 4-octylphenyl or 4-dodecylphenyl.

R as phenylalkyl preferably contains 7-9 C-atoms and is e.g. benzyl, 1-phenylethyl, 2-phenylethyl, α,α-dimethylbenzyl or 3-phenylpropyl.

R as halogen is preferably fluorine, chlorine or bromine.

When R is —COOalkyl, the alkyl group preferably has 1 to 4 C-atoms.

R as an amino group or carbamoyl group preferably has up to 20 C-atoms. Examples are —NH$_2$, —NHCH$_3$, —NHC$_2$H$_5$, —NHCH$_2$CH$_2$OH, —NHC$_{20}$H$_{41}$, —NH-cyclohexyl, —NH-phenyl, —N(CH$_3$)$_2$, —N(n-C$_4$H$_9$)$_2$, —N(CH$_2$CH$_2$OH)$_2$, —N(CH$_3$)(benzyl), morpholino, piperidino, —CONH$_2$, —CONH-phenyl, —CONHC$_8$H$_{17}$, —CON(C$_2$H$_5$)$_2$, —CON(CH$_2$CH$_2$OH)$_2$, morpholinocarbonyl or piperidinocarbonyl.

It is preferred that one of the substituents R is hydrogen, C$_1$–C$_4$ alkyl, C$_1$–C$_4$ alkoxy or amino and that the other three groups R are each hydrogen. It is particularly preferred that all four groups R are simultaneously hydrogen.

When the group R$^o$, $Z_1$ or $Z_2$ is C$_1$–C$_{18}$ alkyl it may be straight or branched chain alkyl, such as methyl, ethyl, n-propyl, iso-propyl, n-butyl, s-butyl, t-butyl, n-pentyl, n-hexyl, n-heptyl, n-octyl, 2-ethyl-hexyl, t-octyl, n-nonyl, n-decyl, n-dodecyl, n-tetradecyl, n-hexadecyl or n-octadecyl group.

When the group $Z_1$ or $Z_2$ is a C$_1$–C$_{18}$ alkyl group optionally interrupted by one or more O, S or NR$^o$ it may be, for example, 2-methoxyethyl, 3-methoxy-propyl, 2-n-butoxyethyl, 2-(2-ethoxy-ethoxy)-ethyl, or 2-n-hexadecyloxy-ethyl, 2-(butylthio)ethyl, 2-(tert.dodecylthio)ethyl, 2-dimethylaminopropyl, 2-dibutylaminoethyl or 2-(methylphenylamino)-ethyl.

When $Z_1$ or $Z_2$ is alkyl substituted by SH, NH$_2$, COOH, COOR$^o$, CONH$_2$, CN or halogen it may be, for example, 2-mercaptopropyl, 3-mercaptopropyl, 2-aminoethyl, 6-aminohexyl, 5-carboxypentyl, 2-carboxyethyl, ethoxycarbonylmethyl, 2-methoxycarbonylethyl, 2-carbamoylethyl, 2-cyanoethyl, 2-chloroethyl or 3-bromopropyl.

When $Z_1$ or $Z_2$ is a C$_2$–C$_{10}$ hydroxyalkyl group optionally interrupted by one or more NR$^o$ groups or oxygen atoms it may be e.g. a hydroxyethyl, hydroxypropyl, hydroxybutyl, hydroxydecyl, hydroxyethoxyethyl or 5-hydroxy-3-(methylaza)-pentyl group.

When the group $Z_1$ or $Z_2$ is a C$_3$–C$_{18}$ straight or branched chain alkenyl group it may be, for example, allyl, methallyl, 2-butenyl, 2-hexenyl or oleyl.

When R$^o$, $Z_1$ or $Z_2$ is a C$_3$–C$_{12}$ optionally substituted cycloalkyl, group, it may be e.g. cyclopropyl, cyclobutyl, cyclopentyl, cyclohexyl, cyclooctyl, cyclododecyl, methylcyclohexyl, 4-hydroxycyclohexyl, 2,4-dimethylcyclohexyl, 4-thiocyclohexyl, 2-ethoxycyclohexyl or 4-chlorocyclohexyl. Preferably it is an unsubstituted C$_5$–C$_8$ cycloalkyl group.

When R$^o$, $Z_1$ or $Z_2$ is a C$_7$–C$_9$ phenylalkyl group it may be, for example, benzyl, 1-phenylethyl, 2-phenylethyl, α,α-dimethyl-benzyl or 3-phenylpropyl.

When R$^o$, $Z_1$ or $Z_2$ is a C$_7$–C$_{18}$ alkylphenyl group it may be, for example, tolyl, xylyl, 4-isopropylphenyl, 4-t-butylphenyl, 4-octylphenyl, or 4-dodecylphenyl.

When R$^o$, $Z_1$ or $Z_2$ is an unsubstituted or substituted aryl group, it may be e.g. phenyl, 3-chlorophenyl, 2,4-dichlorophenyl, 4-nitrophenyl, 3-hydroxyphenyl, 4-methoxyphenyl, 3-isopropoxyphenyl, 4-(methylthio)-phenyl, 4-carboxyphenyl, 1-naphthyl or 4-chloro-1-naphthyl.

R$^o$ is preferably hydrogen or C$_1$–C$_4$ alkyl and $Z_1$ and $Z_2$ are preferably H, C$_1$–C$_{12}$ alkyl, C$_2$–C$_4$ hydroxyalkyl, C$_3$–C$_{12}$ alkoxyalkyl, cyclohexyl, benzyl, phenyl, tolyl or naphthyl or $Z_1$ and $Z_2$ together are tetra- or pentamethylene or 3-oxapentamethylene.

Component (B) of the compositions of the invention is preferably a saturated or unsaturated aliphatic- or cycloaliphatic mono-, di-, tri- or tetra-carboxylic acid amide, imide or nitrile (each as hereinbefore defined) substituted by one group of formula I.

Preferred components (B) are compounds of the formula II:

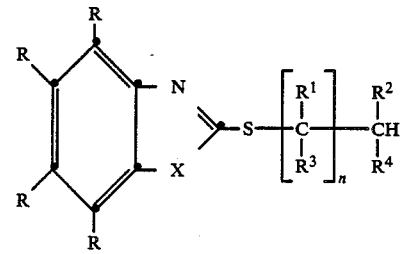

in which X and R have their previous significance; n is 0 or 1; and R$^1$, R$^2$, R$^3$ and R$^4$, independently, are hydrogen, alkyl, hydroxyalkyl, haloalkyl, alkoxyalkyl, optionally mono- or di-substituted phenyl or phenylalkyl, cyano, cyanoalkyl, —COOH, —CONZ$_1$Z$_2$ or alkyl substituted by 1, 2 or 3 groups —COOH or —CONZ$_1$Z$_2$, or corresponding imides containing a group of formula III or IIIa or when n is 1, R$^1$ and R$^2$, or R$^1$ and R$^3$, together form an optionally branched alkylene group optionally substituted by one or two groups —COOH or $CONZ_1Z_2$, or $R^1$ and $R^2$ together constitute a direct bond; whereby the residue $$\{C(R^1)(R^3)\}_nCH(R^2)(R^4)$$

contains at least one group —$CONZ_1Z_2$, cyano or a group of formula III or IIIa and non-toxic base addition salts of compounds of formula II which contain a free carboxyl group.

$R^1$, $R^2$, $R^3$ and $R^4$ as alkyl are preferably $C_1$-$C_{18}$ alkyl e.g. methyl, ethyl, n-propyl, isopropyl, n-butyl, isobutyl, tert.-butyl, n-pentyl, n-hexyl, n-octyl, n-dodecyl or n-octadecyl. As hydroxyalkyl, halogenalkyl or cyanoalkyl these substituents preferably have 1–4 C-atoms e.g. hydroxymethyl, 1- or 2-hydroxyethyl, 2- or 3-hydroxypropyl, chloromethyl, bromoethyl, bromoisopropyl, cyanomethyl or 2-cyanoethyl. As alkoxyalkyl, these substituents preferably having 2–10 C-atoms e.g. methoxymethyl, 1-methoxyethyl, 2-ethoxypropyl, 1-methoxybutyl, n-butoxymethyl or 4-isopropoxybutyl.

When $R^1$, $R^2$, $R^3$ or $R^4$ is alkyl substituted by 1, 2 or 3 groups —COOH or —$CONZ_1Z_2$ it has preferably 2–12 C-atoms and may be, for example, —$CH_2COOH$, —$CH_2CH_2COOH$, —$CH(CH_3)CH_2COOH$, —$(CH_2)_3COOH$, —$(CH_2)_4COOH$, —$(CH_2)_5COOH$, —$CH_2CONH_2$, —$CH_2CONHC_4H_9$, —$CH_2CONHC_8H_{17}$, —$CH_2CON(CH_3)_2$, —$CH_2CH_2CONH_2$, —$CH_2CH_2CONHCH_3$, —$CH_2CH_2CONHC_{12}H_{25}$, —$(CH_2)CONHC_6H_{13}$, —$(CH_2)_3CONHcyclohexyl$, —$CH_2CONHphenyl$, —$CH(COOH)$—$CH_2$—$CONHC_8H_{17}$, —$CH(CONHC_4H_9)$—$CH_2$—$CONHC_4H_9$, —$CH(COOH)$—$CH_2$—$CON)C_2H_5)_2$, —$CH(COOH)$—$CH(CONHbenzyl)$—$CH_2COOH$ or

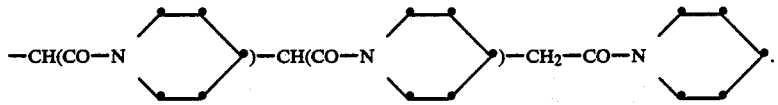

When $R^1$, $R^2$, $R^3$ and $R^4$ are phenyl or phenylalkyl groups, the respective phenyl moieties in the groups may be mono- or di-substituted by halogen, nitro, 1–4 C-alkyl, 1–4 C-alkoxy, carboxy or hydroxy, examples being 4-chlorophenyl, 3-nitrophenyl, tolyl, xylyl, 3-methoxyphenyl, 4-isopropylphenyl, 3-carboxyphenyl, 4-hydroxyphenyl, 4-bromobenzyl, 4-tert.-butylbenzyl, 2-phenylethyl or 3-phenylpropyl, but preferably phenyl or benzyl.

When $R^1$ and $R^2$, or $R^1$ and $R^3$ together are alkylene, then they form, together with the C-atoms to which they are bonded, a cycloalkane ring, preferably a cyclopentane or cyclohexane ring which may be substituted by alkyl groups, especially $C_1$-$C_4$ alkyl groups, or by one or two groups —CN, —COOH or $CONZ_1Z_2$.

When $R^1$ and $R^2$ together denote a direct bond, the compounds of formula II are unsaturated caboxylic acid amides, imides or nitriles.

Preferred compounds II are those in which $R^1$, $R^2$, $R^3$ and $R^4$ and H, $C_1$-$C_4$ alkyl, CN, —COOH —$CONZ_1Z_2$ or alkyl substituted by —CN, —COOH or —$CONZ_1Z_2$. More preferred are compounds in which $R^4$ is —COOH, —$CONZ_1Z_2$ or $C_1$-$C_4$-alkyl substituted by —COOH or —$CONZ_2Z_1$.

Most preferred are compounds of formula II in which n is 1 and at least two of $R^1$, $R^2$, $R^3$ and $R^4$ are —COOH, —$CONZ_1Z_2$ or alkyl substituted by —COOH on —$CONZ_1Z_2$.

Most preferred are compounds of formula II containing two groups —$CONZ_1Z_2$ or one —$CONZ_1Z_2$ and one —COOH group on adjacent carbon atoms.

Base addition non-toxic salts are metal-, ammonium- and organic ammonium salts, especially salts of alkali metals, alkaline earth metals, metals of groups IIB, IIIA or VIII of the Periodic System of Elements, ammonium salts or salts of organic amines. Examples are, especially, sodium-, potassium-, calcium-, magnesium-, zinc-, aluminium-, ammonium-, trialkylammonium- and tri(hydroxyethyl)ammonium salts.

Specific examples of compounds of formula I include:
N-methyl benzothiazol-2-ylthio acetamide
N-phenyl benzothiazol-2-ylthio acetamide
N-ethyl(5-trifluoromethylbenzothiazol-2-ylthio)acetamide
N-n-propyl(5-carboxybenzothiazol-2-ylthio)acetamide
N-n-octyl(5-ethoxycarbonylbenzothiazol-2-ylthio)acetamide
N-n-dodecyl(6-methylsulphonylbenzothiazol-2-ylthio)acetamide
N-ethyl 3-(benzothiazol-2-ylthio)propionamide
N-allyl 3-(benzothiazol-2-ylthio)propionamide
N-cyclohexyl 3-(benzothiazol-2-ylthio)propionamide
N-n-octadecyl 3-(benzothiazol-2-ylthio)propionamide
N-methyl 3-(6-aminobenzothiazol-2-ylthio)propionamide
N-cyclohexyl 3-(6-aminobenzothiazol-2-ylthio)propionamide
N-ethyl 3-(benzothiazol-2-ylthio)-2-methyl propionamide
N-iso-butyl 4-(benzothiazol-2-ylthio)butyramide
N-ethyl 3-(benzothiazol-2-ylthio)butyramide
N-2-ethylhexyl 3-(benzothiazol-2-ylthio)butyramide
N-2-methoxyethyl 3-(benzothiazol-2-ylthio)-3-methyl butyramide
N,N'-diisopropyl benzothiazol-2-ylthio malonamide
N,N'-dimethyl benzothiazol-2-ylthio succinamide
N,N'-diethyl benzothiazol-2-ylthio succinamide
N,N'-diisopropyl benzothiazol-2-ylthio succinamide
N,N'-di-n-butyl benzothiazol-2-ylthio succinamide
N,N'-di-i-octyl benzothiazol-2-ylthio succinamide
N,N'-di-n-decyl benzothiazol-2-ylthio succinamide
N,N'-di-n-octadecyl benzothiazol-2-ylthio succinamide
N,N'-di-2-ethylhexyl benzothiazol-2-ylthio succinamide
N,N'-dicyclohexyl benzothiazol-2-ylthio succinamide
N,N'-diphenyl benzothiazol-2-ylthio succinamide
N,N'-dibenzyl benzothiazol-2-ylthio succinamide
N,N'-di-(4-methylphenyl)benzothiazol-2-ylthio succinamide
N,N'-butyl methyl benzothiazol-2-ylthio succinamide
N-methyl N'-phenyl benzothiazol-2-ylthio succinamide
N-ethyl N'-benzyl benzothiazol-2-ylthio succinamide
1-(benzothiazol-2-ylthio)-2-methylcarbamoyl-ethane-1-carboxylic acid
1-(benzothiazol-2-ylthio)-1-ethylcarbamoyl-ethane-2-carboxylic acid
1-(benzothiazol-2-ylthio)-1-ethylhexylcarbamoyl-ethane-2-carboxylic acid
N,N'-di-n-propyl(5-methylbenzothiazol-2-ylthio)succinamide N,N'-di-n-hexyl(6-ethylbenzothiazol-2-ylthio) succinamide
N,N'-di-but-3-enyl (4-isopropylbenzothiazol-2-ylthio)succinamide
N-methyl N'-allyl(7-t-butylbenzothiazol-2-ylthio)succinamide
N,N'-dipentyl(5-n-hexylbenzothiazol-2-ylthio)succinamide
N,N'-dicyclopentyl(6-[1,1,3,3-tetramethylbutyl]-benzothiazol-2-ylthio)succinamide
N,N'-diphenyl(6-cyclohexylbenzothiazol-2-ylthio)succinamide
N,N'-di-naphthyl(7-benzylbenzothiazol-2-ylthio)succinamide
N,N'-dibenzyl(6-methoxybenzothiazol-2-ylthio)succinamide
N-ethyl N'-methyl(5-methoxybenzothiazol-2-ylthio)succinamide
N-benzyl N'-phenyl(5-ethoxycarbonylbenzothiazol-2-ylthio)succinamide
1-(4-methylbenzothiazol-2-ylthio)-2-methylcarbamoylethane-1-carboxylic acid
1-(6-methylbenzothiazol-2-ylthio)-2-butylcarbamoylethane-2-carboxylic acid
N,N'-di-1,1,3,3-tetramethylbutyl(4-fluorobenzothiazol-2-ylthio)succinamide
N,N'-dioctadecyl(7-bromobenzothiazol-2-ylthio)succinamide
N,N'-di-n-nonyl(6-chlorobenzothiazol-2-ylthio)succinamide
N,N'-dimethyl(4-phenylbenzothiazol-2-ylthio)succinamide
N,N'-diethyl(6-nitrobenzothiazol-2-ylthio)succinamide
N,N'-diisopropyl(5-cyanobenzothiazol-2-ylthio)succinamide
N,N'-di-iso-butyl(5-carboxybenzothiazol-2-ylthio)succinamide
N,N'-di-n-hexyl(7-hydroxybenzothiazol-2-ylthio)succinamide
N,N'-di-ethoxyethyl(6-chloro-4-methylbenzothiazol-2-ylthio)succinamide
1-(5-chloro-6-n-butylbenzothiazol-2-ylthio)-2-n-octylcarbamoylethane-2-carboxylic acid
1-(4-bromo-5-benzylbenzothiazol-2-ylthio)-2-benzylcarbamoylethane-2-carboxylic acid
1-(5-nitro-6-n-propylbenzothiazol-2-ylthio)-2-phenylcarbamoylethane-2-carboxylic acid
1-(5-bromo-6-n-propoxybenzothiazol-2-ylthio)-2-naphthylcarbamoylethane-3-carboxylic acid
1-(6-amino-benzothiazol-2-ylthio)-2-allylcarbamoylethane-2-carboxylic acid
1-(6-methylaminobenzothiazol-2-ylthio)-2-cyclohexylcarbamoylethane-2-carboxylic acid
1-(5-dimethylaminobenzothiazol-2-ylthio)-2-methoxyethylcarbamoylethane-2-carboxylic acid
1-(7-phenylaminobenzothiazol-2-ylthio)-2-n-octylcarbamoyl-ethane-2-carboxylic acid
1-(6-diphenylaminobenzothiazol-2-ylthio)-2-n-decylcarbamoyl-ethane-2-carboxylic acid
1-(4-benzylaminobenzothiazol-2-ylthio)-2-n-octadecylcarbamoylethane-2-carboxylic acid
N,N'-dimethyl(4-morpholinobenzothiazol-2-ylthio)succinamide
N,N'-diethyl(5-carbamoylbenzothiazol-2-ylthio)succinamide
N,N'-di-n-propyl(5-methylcarbamoylbenzothiazol-2-ylthio)succinamide
N,N'-di-n-butyl(5-diethylcarbamoylbenzothiazol-2-ylthio)succinamide
N,N'-di-1,1,3,3-tetramethylbutyl(6-phenylcarbamoylbenzothiazol-2-ylthio)succinamide
N,N'-diphenyl(5,6-dimethyl-benzothiazol-2-ylthio)succinamide
N,N'-dibenzyl(4,5,6-triethylbenzothiazol-2-ylthio)succinamide
N,N'-diethyl(4,5,6,7-tetramethylbenzothiazol-2-ylthio)succinamide
N,N'-diethyl(benzothiazol-2-ylthio)-propane-1,2-dicarboxylic acid amide
N,N'-diethyl 3-(benzothiazol-2-ylthio)-propane-1,2-dicarboxylic acid amide
1-(benzothiazol-2-ylthio)-3-ethylcarbamoyl-propane-2-carboxylic acid
N,N'-dimethyl 3-(6-trifluoromethylbenzothiazol-2-ylthio)-propane-1,2-dicarboxylic acid amide
N,N'-di-n-butyl 3-(6-carbmethoxybenzothiazol-2-ylthio)-propane-1,2-dicarboxylic acid amide
N,N'-di-n-octyl 3-(6-aminobenzothiazol-2-ylthio)-propane-1,2-dicarboxylic acid amide
N,N'-dibenzyl 3-(5-ethylaminobenzothiazol-2-ythio)-propane-1,2-dicarboxylic acid amide
N-methyl N'-octadecyl 3-(4-dibutylaminobenzothiazol-2-ylthio)-propane-1,2-dicarboxylic acid amide
N,N'-diphenyl 4-(morpholinobenzothiazol-2-ylthio)-propane-1,2-dicarboxylic acid amide
N,N'-diethyl 1-(benzothiazol-2-ylthio)-propane-1,3-dicarboxylic acid amide
N,N'-diisopropyl 2-(benzothiazol-2-ylthio)-propane-1,3-dicarboxylic acid amide
N,N'-dimethyl 3-(benzothiazol-2-ylthio)-3-phenylpropane-1,2-dicarboxylic acid amide
N,N'-diethyl 3-(benzothiazol-2-ylthio)-3-(4-carboxyphenyl)-propane-1,2-dicarboxylic acid amide
N,N'-di-n-butyl 3-(benzothiazol-2-ylthio)-3-(2,4-dicarboxyplhenyl)-propane-1,2-dicarboxylic acid amide
N,N'-di-n-hexyl 3-(benzothiazol-2-ylthio)-3,3-diphenylpropane-1,2-dicarboxylic acid amide
N,N'-dimethyl 1-(benzothiazol-2-ylthio)-butane-1,2-dicarboxylic acid amide
N,N'-dibenzyl 1-(benzothiazol-2-ylthio)-2-methylpropane-1,2-dicarboxylic acid amide
N,N'-di-allyl 2-(benzothiazol-2-ylthio)-butane-2,3-dicarboxylic acid amide
N,N'-diphenyl 1-(benzothiazol-2-ylthio)-butane-2,4-dicarboxylic acid amide
N,N',N''-trimethyl 4-(benzothiazol-2-ylthio)-butane-1,2,3-tricarboxylic acid amide
1-(benzothiazol-2-ylthio)-3,4-bis(methylcarbamoyl)-butane-2-carboxylic acid
N,N'-diethyl 1-(benzothiazol-2-ylthio)-pentane-1,5-dicarboxylic acid amide
N,N'-di-n-hexyl 3-(benzothiazol-2-ylthio)-hexane-1,2-dicarboxylic acid amide
N,N',N'',N'''-tetraethyl 8-(benzothiazol-2-ylthio)-octane-1,3,5,7-tetracarboxylic acid amide
N,N'-dimethyl 1-(benzothiazol-2-ylthio)-cyclohexane-1,2-dicarboxylic acid amide
N,N'-diphenyl 4-(benzothiazol-2-ylthio)-cyclohexane-1,2-dicarboxylic acid amide
N,N',N''-tri-n-octyl 1-(benzothiazol-2-ylthio)-propane-1,2,3-tricarboxylic acid amide
N,N'-di-n-pentyl 1-(benzothiazol-2-ylthio)-3-chloropropane-1,2-dicarboxylic acid amide
N,N'-di-n-nonyl 1-(benzothiazol-2-ylthio)-3-methoxypropane-1,2-dicarboxylic acid amide N,N'-di-n-decyl 1-(benzothiazol-2-ylthio)-3-methoxypropane-1,2-dicarboxylic acid amide
N,N'-dimethyl 1-(benzothiazol-2-ylthio)-2-phenyl succinamide
N,N'-diethyl 1-(benzothiazol-2-ylthio)-2-benzyl succinamide
N,N-diethyl 2,3-bis-(benzothiazol-2-ylthio)-butane-1,4-dicarboxylic acid amide
sodium 1-(benzothiazol-2-ylthio)-2-methylcarbamoyl-ethane-1-carboxylate
potassium 1-(benzothiazol-2-ylthio)-2-ethylcarbamoyl-ethane-2-carboxylate
calcium 1-(benzothiazol-2-ylthio)-2-ethylcarbamoyl-ethane-2-carboxylate
zinc 1-(benzothiazol-2-ylthio)-2-isopropylethane-2-carboxylate
cobalt 1-(benzothiazol-2-ylthio)-2-n-butylcarbamoyl-ethane-2-carboxylate
aluminium 1-(benzothiazol-2-ylthio)-2-ethoxycarbamoyl-ethane-2-carboxylate
ammonium 1-(benzothiazol-2-ylthio)-2-n-octylcarbamoyl-ethane-2-carboxylate
methylammonium 1-(benzothiazol-2-ylthio)-2-methylcarbamoyl-ethane-2-carboxylate
triethanolammonium 1-(benzothiazol-2-ylthio)-2-methylcarbamoylethane-2-carboxylate
octylammonium 1-(benzothiazol-2-ylthio)-2-phenylcarbamoylethane-2-carboxylate
cyclohexylammonium 1-(benzothiazol-2-ylthio)-2-benzylcarbamoylethane-2-carboxylate
diethyammonium 1-(benzothiazol-2-ylthio)-2-n-butylcarbamoylethane-2-carboxylate
tributylammonium 1-(benzothiazol-2-ylthio)-2-methylcarbamoylethane-2-carboxylate
sodium 3-(benzothiazol-2-ylthio)-2-ethylcarbamoyl-propane-1,2-dicarboxylate
potassium 3-(benzothiazol-2-ylthio)-2-n-propylcarbamoyl-propane-1,2-dicarboxylate
calcium 3-(benzothiazol-2-ylthio)-2-methylcarbamoyl-propane-1,2-dicarboxylate
zinc 3-(benzothiazol-2-ylthio)-2-benzylcarbamoyl-propane-1,2-dicarboxylate
aluminium 3-(benzothiazol-2-ylthio)-2-phenylcarbamoyl-propane-1,2-dicarboxylate
ammonium 3-(benzothiazol-2-ylthio)-2-allylcarbamoyl-propane-1,2-dicarboxylate
N-methyl benzoxazol-2-ylthio acetamide
N-ethyl (6-aminobenzoxazol-2-ylthio) acetamide
N-isopropyl 3-(benzoxazol-2-ylthio)-propionamide
N-n-dodecyl 4-(benzoxazol-2-ylthio)-butyramide
N,N'-diethyl benzoxazol-2-ylthio malonamide
N,N'-diethyl benzoxazol-2-ylthio succinamide
N,N'-diisopropyl benzoxazol-2-ylthio succinamide
N,N'-di-t-butyl benzoxazol-2-ylthio succinamide
N,N'-di-n-decyl benzoxazol-2-ylthio succinamide
N,N'-di-n-octadecyl benzoxazol-2-ylthio succinamide
N,N'-di-2-ethylhexyl benzoxazol-2-ylthio succinamide
N,N'-dicyclohexyl benzoxazol-2-ylthio succinamide
N,N'-diphenyl benzoxazol-2-ylthio succinamide
N,N'-dibenzyl benzoxazol-2-ylthio succinamide
N,N'-di-(4-methylphenyl) benzoxazol-2-ylthio succinamide
N-butyl N'-methyl benzoxazol-2-ylthio succinamide
N-methyl N'-phenyl benzoxazol-2-ylthio succinamide
N-ethyl N'-benzyl benzoxazol-2-ylthio succinamide
1-(benzoxazol-2-ylthio)-2-methylcarbamoyl-ethane-1-carboxylic acid
1-(benzoxazol-2-ylthio)-1-ethylcarbamoyl-ethane-2-carboxylic acid
1-(benzoxazol-2-ylthio)-2-ethylhexylcarbamoyl-ethane-1-carboxylic acid
N,N'-diethyl 3-(benzoxazol-2-ylthio)-propane-1,2-dicarboxylic acid amide
N,N'-dimethyl 1-(benzoxazol-2-ylthio)-butane-1,2-dicarboxylic acid amide
N,N',N''-triethyl 4-(benzoxazol-2-ylthio)-butane-1,2,3-tricarboxylic acid amide
N,N'-di-n-propyl 1-(benzoxazol-2-ylthio)-pentane-1,5-dicarboxylic acid amide
N,N'-di-n-octyl 3-(benzoxazol-2-ylthio)-hexane-1,2-dicarboxylic acid amide
N,N',N'',N'''-tetramethyl 8-(benzoxazol-2-ylthio)-octane-1,3,5,7-tetracarboxylic acid amide
N,N'-diethyl 2,3-bis-(benzoxazol-2-ylthio)-butane-1,4-dicarboxylic acid amide
zinc 1-(benzoxazol-2-ylthio)-2-methylcarbamoylethane-1-carboxylate
ammonium 1-(benzoxazol-2-ylthio)-2-ethylcarbamoyl-ethane-1-carboxylate
N-methyl benzimidazol-2-ylthio acetamide
N-ethyl (5 (or 6)-carboxybenzimidazol-2-ylthio) acetamide
N-(5 (or 6)-ethoxycarbonylbenzimidazol-2-ylthio) acetamide
N-ethyl (5 (or 6)-aminobenzimidazol-2-ylthio) acetamide
N-phenyl 3-(benzimidazol-2-ylthio) propionamide
N-allyl 4-(benzimidazol-2-ylthio) butyramide
N-benzyl 3-(benzimidazol-2-ylthio) butyramide
benzimidazol-2-ylthio malonamide
N,N'-diethylbenzimidazol-2-ylthio succinamide
N,N'-diisopropyl benzimidazol-2-ylthio succinamide
N,N'-di-t-butyl benzimidazol-2-ylthio succinamide
N,N'-di-n-decyl benzimidazol-2-ylthio succinamide
N,N'-di-n-octadecyl benzimidazol-2-ylthio succinamide
N,N'-di-2-ethylhexyl benzimidazol-2-ylthio succinamide
N,N'-dicyclohexyl benzimidazol-2-ylthio succinamide
N,N'-diphenyl benzimidazol-2-ylthio succinamide
N,N'-dibenzyl benzimidazol-2-ylthio succinamide
N,N'-di-(4-methylphenyl) benzimidazol-2-ylthio succinamide
N-butyl N'-methyl benzimidazol-2-ylthio succinamide
N-methyl N'-phenyl benzimidazol-2-ylthio succinamide
N-ethyl N'-benzyl benzimidazol-2-ylthio suuccinamide
1-(benzimidazol-2-ylthio)-2-methylcarbamoyl-ethane-1-carboxylic acid
1-(benzimidazol-2-ylthio)-1-ethylcarbamoyl-ethane-2-carboxylic acid
1-(benzimidazol-2-ylthio)-2-ethylhexylcarbamoyl-ethane-2-carboxylic acid
N,N'-diethyl (6 (or 5)-ethylbenzimidazol-2-ylthio) succinamide
N,N'-dimethyl (7 (or 4)-benzylbenzimidazol-2-ylthio) succinamide
N,N'-di-allyl (5 (or 6)-ethoxycarbonylbenzimidazol-2-ylthio) succinamide
N,N'-dibenzyl (6 (or 5)-ethoxybenzimidazol-2-ylthio) succinamide
N,N'-diphenyl (5 (or 6)-chlorobenzimidazol-2-ylthio) succinamide
N,N'-dimethyl 1-(benzimidazol-2-ylthio)-2-phenyl succinamide
N,N'-diethyl 1-(benzimidazol-2-ylthio)-2-benzyl succinamide N,N'-di-n-butyl (5 (or 6)-chloro-4 (or 7)-methylbenzimidazol-2-ylthio) succinamide
(5,6-dimethylbenzimidazol-2-ylthio) succinamide
N-butyl N'-methyl (4,5,6-triethylbenzimidazol-2-ylthio) succinamide
N,N'-di-n-hexyl (4,5,6,7-tetramethylbenzimidazol-2-ylthio) succinamide
N,N'-di-2-ethylhexyl (1-benzimidazol-2-ylthio)-propane-1,2-dicarboxylic acid amide
N,N'-dimethyl 3-(benzimidazol-2-ylthio)-propane-1,2-dicarboxylic acid amide
N,N'-diethyl 1-(benzimidazol-2-ylthio)-butane-1,2-dicarboxylic acid amide
N,N',N''-trimethyl 4-(benzimidazol-2-ylthio)-butane-1,2,3-tricarboxylic acid amide
N,N'-dibenzyl 1-(benzimidazol-2-ylthio)-2-methylpropane-1,2-dicarboxylic acid amide
N,N'-diisopropyl 2-(benzimidazol-2-ylthio)-butane-2,3-dicarboxylic acid amide
N,N'-diphenyl 1-(benzimidazol-2-ylthio)-pentane-1,5-dicarboxylic acid amide
N,N'-dibenzyl 3-(benzimidazol-2-ylthio)-hexane-1,2-dicarboxylic acid amide
N,N',N'',N'''-tetramethyl 8-(benzimidazol-2-ylthio)-octane-1,3,5,7-tetracarboxylic acid amide
N,N'-di-n-hexyl 1-(benzimidazol-2-ylthio)-cyclohexane-1,2-dicarboxylic acid amide
N,N',N''-triethyl 1-(benzimidazol-2-ylthio)-propane-1,2,3-tricarboxylic acid amide
N,N'-dimethyl 2,3-bis-(benzimidazol-2-ylthio)-butane-1,4-dicarboxylic acid amide
calcium 1-(benzimidazol-2-ylthio)-2-methylcarbamoyl-ethane-1-carboxylate
zinc 1-(benzimidazol-2-ylthio)-2-ethylcarbamoyl-ethane-1-carboxylate
ammonium 1-(benzimidazol-2-ylthio)-2-isopropylcarbamoyl-ethane-1-carboxylate
tributylammonium 1-(benzimidazol-2-ylthio)-2-n-octylcarbamoylethane-1-carboxylate
sodium 3-(benzimidazol-2-ylthio)-2-ethylcarbamoyl-ethane-1-carboxylate
calcium 3-(benzimidazol-2-ylthio)-2-isopropylcarbamoyl-ethane-1-carboxylate
zinc 3-(benzimidazol-2-ylthio)-2-n-hexylcarbamoyl-ethane-1-carboxylate
N,N'-dimethyl (benzimidazol-2-ylthio)-ethene-1,2-dicarboxylic acid amide
N,N'-diethyl (benzimidazol-2-ylthio)-ethane-1,2-dicarboxylic acid amide
N,N'-diethyl (benzoxazol-2-ylthio)-ethane-1,2-dicarboxylic acid amide
N,N'-Diisopropyl 1-(benzothiazol-2-ylthio)-propene-1,2-dicarboxylic acid amide
N,N'-di-n-butyl 2-(benzothiazol-2-ylthio)-but-1-ene-2,3-dicarboxylic acid amide
benzothiazol-2-ylthio succinimide
5-methylbenzothiazol-2-ylthio succinimide
6-aminobenzothiazol-2-ylthio succinimide
5,6-dimethylbenzothiazol-2-ylthio succinimide
4,5,6-triethylbenzothiazol-2-ylthio succinimide
4,5,6,7-tetramethylbenzothiazol-2-ylthio succinimide
benzoxazol-2-ylthio succinimide
benzimidazol-2-ylthio succinimide
3-(benzothiazol-2-ylthio)-propane-1,2-dicarboxylic imide
3-(benzoxazol-2-ylthio)-propane-1,2-dicarboxylic imide
3-(benzimidazol-2-ylthio)-propane-1,2-dicarboxylic imide
4-(benzothiazol-2-ylthio)-3-ethoxycarbonyl-butane-1,2-dicarboxylic imide
N-methyl benzothiazol-2-ylthio succinimide
N-n-octyl benzothiazol-2-ylthio succinimide
N-phenyl benzothiazol-2-ylthio succinimide
N-methyl 3-(benzothiazol-2-ylthio)-propane 1,2-dicarboxylic imide
N-n-dodecyl 3-(benzothiazol-2-ylthio)-propane-1,2-dicarboxylic imide
benzothiazol-2-ylthio-acetonitrile
2-(benzothiazol-2-ylthio)-propionitrile
benzothiazol-2-ylthio-succinodinitrile
benzothiazol-2-ylthio-malodinitrile
3-benzothiazol-2-ylthio-propane-1,2-dinitrile
N,N,N',N'-tetraethyl benzothiazol-2-ylthio succinamide
N,N,N',N-tetra-n-octyl benzothiazol-2-ylthio succinamide
N-hydroxyethyl benzothiazol-2-ylthio acetamide
N-hydroxyethyl 3-(benzothiazol-2-ylthio) propionamide
N,N'-bis(hydroxyethyl)benzothiazol-2-ylthio succinamide
N,N'-bis(morpholino)benzothiazol-2-ylthio succinamide
1-(benzothiazol-2-ylthio)-2-(hydroxyethylcarbamoyl)ethane
1-carboxylic acid
1-(benzothiazol-2-ylthio)-3-(hydroxyethylcarbamoyl) propane-2-carboxylic acid
1-(benzothiazol-2-ylthio)-2-(diethylcarbamoyl)ethane 1-carboxylic acid
1-(benzothiazol-2-ylthio)-3-(dicyclohexylcarbamoyl) propane
2-carboxylic acid Some of the compounds useful as components (B) of the claimed compositions are known.

Thus, compounds having the formula:

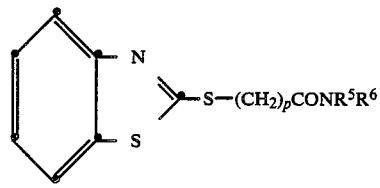

in which p is 1 or 2;
and, when p is 1, $R^5$ and $R^6$ are each benzyl, or $R^5$ is H and $R^6$ is phenyl, p-tolyl, benzyl, o-methoxyphenyl, m-nitrophenyl, phenylethyl or 1-decyl, or $R^5$ is methyl and $R^6$ is phenyl or $R^5R^6N$— is morpholino or piperidino;
and, when p is 2, $R^5$ and $R^6$ are each methyl or are each ethyl, or $R^5R^6N$ is morpholino, are described in Ann. Ist. Super. Sanita 1967 3(Pt 3-4) 392–4, ref. Chem. Abstr. 69 (1968), 96541a.

Moreover, the preparation of N-hydroxyethyl-1-benzothiazol-2-ylthio acetamide is described in Rev. Roum. Chim. 28 (1983), 757–62.

The compound 2-(benzimidazol-2-ylthio) propionitrile is described in Chemical Abstracts 83 (1975), 79146 a.

On the other hand, most of the compounds used as components (B) are novel compounds and, as such, form part of the present invention.

One preferred group of novel compounds is that of formula II

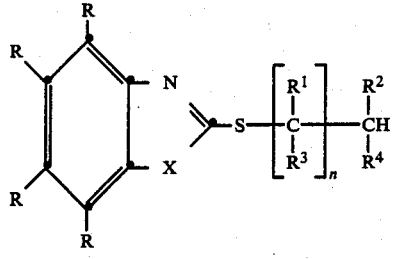

wherein R, n, X, $R^1$, $R^2$, $R^3$ and $R^4$ have their previous signifcance provided that the residue

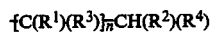

contains 2, 3 or 4 groups —$CONZ_1Z_2$ in which $Z_1$ and $Z_2$ have their previous significance.

Another preferred group of novel compounds are the partial amides viz. compounds of formula II in which R, n, X, $R^1$, $R^2$, $R^3$ and $R^4$ have their previous significance provided that the residue

contains at least one group —$CONZ_1Z_2$ and at least one group —COOH.

Other preferred novel compounds are the imides of formula II in which R, $R^2$ and $R^4$, have their previous significance, n is 1, $R^1$ and $R^2$ are H, provided the residue

contains a group of formula III or IIIa.

Other less preferred novel compounds are the cyano compounds of formula II in which R, X, n, $R^1$, $R^2$, $R^3$, $R^4$ have their previous significance and the residue

contains 2, 3 or 4 cyano groups.

The components (B), whether they be known or novel compounds can be prepared by various processes.

One preferred process is that which is the subject-matter of a separate patent application, now U.S. Pat. No. 4,652,653, namely the reaction of compounds of formula:

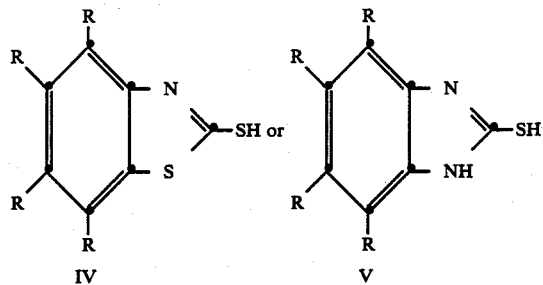

with an unsaturated carboxylic acid amide, imide or nitrile of formula:

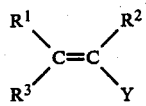

wherein $R^1$, $R^2$ and $R^3$ have their previous significance and Y is —CN, —$CONZ_1Z_2$ or is linked in an imide bond —CO—N($Z_1$)—CO— wherein $Z_1$ and $Z_2$ have their previous significance, in a strongly acid medium.

Another process for producing components (B) is that described in a separate patent application Ser. No. 610,146 in which, preferably in the presence of a base, (a) a compound of formula:

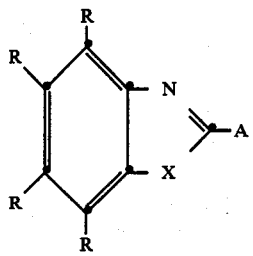

in which R and X have their previous significance and A is a leaving group e.g. Cl, Br, I or p-Tosyloxy, is reacted with a compound of formula:

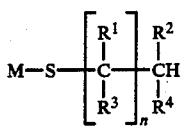

in which $R^1$ to $R^4$ and n have their previous significance and M is hydrogen or a cation e.g. an alkali metal-, alkaline earth metal- or ammonium cation; or (b) a compound of formula:

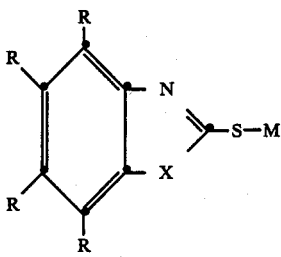

is reacted with a compound of formula:

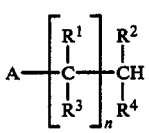

A third method of producing components (B) which are full amides comprises amidating the corresponding free carboxylic acids or their esters or halides with an amine $HNZ_1Z_2$ wherein $Z_1$ and $Z_2$ have their previous significance;

Partial amides may be obtained e.g. by reaction of a cyclic anhydride with one equivalent of an amine $HNZ_1Z_2$ in which $Z_1$ and $Z_2$ have their previous significance.

Nitrile components (B) may be obtained by dehydrating the corresponding amides using conventional dehydrating agents.

Imide components (B) may be obtained by reacting a cyclic anhydride with one equivalent or an amine $Z_1NH_2$ wherein $Z_1$ has its previous significance.

Especially valuable as cyclic anhydrides for use in producing partial amide or imide components (B), are compounds having the formula:

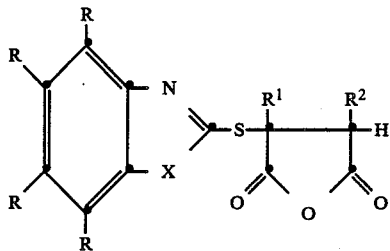

X and the formula:

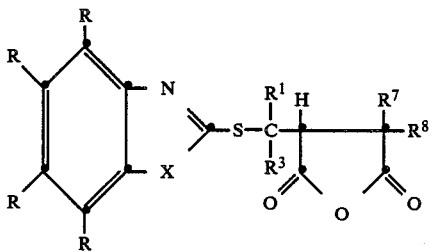

XI in which R, X, $R^1$, $R^2$ and $R^3$ have their previous significance and $R^7$ and $R^8$ are hydrogen or $C_1$-$C_{10}$alkyl which may be substituted by —COOH or —$CONZ_1Z_2$ and the number of C-atoms in $R^7$ and $R^8$ does not exceed 10. Preferably in X and XI the substituents $R^1$, $R^2$, $R^3$, $R^7$ and $R^8$ are hydrogen.

The cyclic anhydrides of formula X and XI are new compounds and, as such, form the subject-matter of a separate application.

The new anhydrides may be prepared by dehydration of the corresponding vicinal carboxylic acids.

Suitable dehydrating agents are acetic anhydride, phosphoryl chloride or carbodiimides such as dicyclohexylcarbodiimide.

The new anhydrides may also be produced by the addition of a compound of formula:

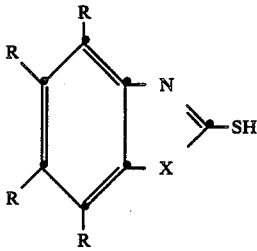

XII wherein R has its previous significance, to a compound of formula XIII or XIV

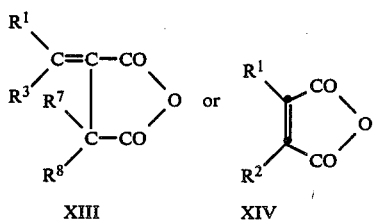

wherein $R^1$, $R^2$, $R^3$, $R^7$ and $R^8$ have their previous significance.

All these compounds containing a group of formula I are useful as corrosion inhibitors in an applicational medium selected from:

(a) surface coatings and (b) wholly or partly aqueous media other than aqueous surface coatings.

With respect to surface coatings (a), the nature of the film-forming binder component of the surface coating composition used will depend upon whether the surface coating has a non-aqueous base. For non-aqueous surface coatings, the binder may be selected from epoxy resins optionally containing a curing agent, polyurethane resins, aminoplast resins, acrylic resins, polyesters and alkyd resins or their mixtures. Other examples of respective binder systems are polyvinyl-butyral, phenolic resins, polyvinyl acetate or its copolymers, polyvinyl chloride or its copolymers, chlorinated rubber or other chlorinated resins, styrene butadiene copolymers, linseed oil and other drying oils and cellulose esters.

For aqueous-based surface coatings, there may be used any desired film-formers known for use as binders for aqueous coating compositions e.g. dispersion paints, emulsion paints or electro-depositable paints. The aqueous binder used may be one or more water-soluble or water-dispersible synthetic resins. Examples of such resins are alkyd, polyester, acrylic, polyurethane, epoxide, phenoplast condensate and aminoplast precondensate resins and mixtures of these resins, and homo- or copolymers of vinyl ethers, vinyl esters, styrene, vinylidene chloride and vinyl chloride.

The water-borne binder may be optionally crosslinked with aminoplast resins, phenoplast resins, blocked isocyanates, epoxy resins, Mannich bases of phenols or activated carboxylic esters.

There are several methods available for rendering these binders suitable for use in water-borne paints. These methods, which are well known to those skilled in the coatings art, include the incorporation of basic or acidic functional groups which are then neutralised prior to dilution with water.

In addition to the components (A) and (B), the coating composition can also contain further components, for example pigments, dyes, extenders and other additives such as are customary for non-aqueous or water-borne coating compositions respectively. The pigments can be organic, inorganic or metallic pigments, for example titanium dioxide, iron oxide, aluminium bronze, phthalocyanine blue etc. It is also possible to use concomitantly anti-corrosion pigments, for example pigments containing phosphates or borates, metal pigments and metal oxide pigments (see Farbe und Lack 88 (1982), 183) or the pigments described in European Pat. No. A 54,267. Examples of extenders which can be used concomitantly are talc, chalk, alumina, baryte, mica or silica. Examples of further additives are flow control auxiliaries, dispersing agents, thioxotropic agents, adhesion promoters, antioxidants, light stabilisers or curing catalysts.

Particular importance attaches to the addition of basic extenders or pigments. in certain binder systems, for example, in acrylic and alkyd resins, these produce a synergistic effect on the inhibition of corrosion. Examples of such basic extenders or pigments are calcium carbonate, magnesium carbonate, zinc oxide, carbonate, zinc phosphate, magnesium oxide, aluminium oxide, aluminium phosphate or mixtures thereof. Examples of pigments are those based on aminoanthraquinone.

The corrosion inhibitors used according to the invention can also first be applied to such basic extenders or pigments, for example by chemisorption from an aqueous solution, and the preparations thus obtained can be added to the coating composition.

In a further preferred embodiment of the invention the corrosion inhibitors are used together with basic ion exchangers or an ion exchanger of this type is first treated with a solution of the inhibitor, and this preparation is then added to the coating composition. Examples of basic ion exchangers are all typical anion exchangers, such as those available commercially, for example under the names Dowex® 1 or 11 or Amberlite® IRA.

Finally, the corrosion inhibitor can also be applied to a neutral carrier. Suitable carriers are, in particular, pulverulent extenders or pigments. This technique is described in greater detail in German Offenlegungsschrift No. 3,122,907.

In addition to the component (B) the coating composition can also contain other organic, metal-organic or inorganic corrosion inhibitors, for example salts of nitroisophthalic acid, tannin, phosphoric esters, technical amines, substituted benzotriazoles or substituted phenols (e.g. p-nonylphenoxyacetic acid), such as are described in German Offenlegungsschrift No. 3,146,265.

The coating compositions according to the invention are preferably used as a primer on metallic substrates, in particular on iron, steel, copper and aluminium. Here they can function as so-called conversion coatings, in that chemical reactions take place at the interface beween the metal and the coating. The coating compositions may also find application in can coating processes. The application of the coatings can be effected by the customary methods, such as spraying, brushing, rollercoating or dipping. One preferred method is electrodeposition which may be either anodic or cathodic, but is preferably cathodic.

Depending on whether the film-former is a resin which dries physically or can be cured by heat or radiation, the curing of the coatings is carried out at room temperature, by stoving or by irradiation.

The corrosion inhibitors can be added to the coating composition during the preparation of the latter, for example during the distribution of the pigment by grinding or the inhibitors are dissolved beforhand in a solvent and the solution is stirred into the coating composition. The inhibitor is used in an amount of 0.1-20% by weight, preferably 0.5-5% by weight, based on the solids content of the coating composition.

The aqueous applicational media (b) may be wholly aqueous or only partly aqueous.

In practice, when the application medium is a wholly or partly aqueous application medium, the amount of component (B) is conveniently within the range of from 0.1 to 50,000 ppm (or 0.00001 to 5% by weight), preferably from 1 to 500 ppm (or 0.0001 to 0.05% by weight), based on the aqueous system.

The inhibitor component B may be used alone or in conjunction with other compounds known to be useful in the treatment of aqueous systems.

In the treatment of systems which are completely aqueous, such as cooling water systems, air-conditioning systems, steamgenerating systems, sea-water evaporator systems, hydrostatic cookers, and closed circuit heating or refrigerant systems, further corrosion inhibitors may be used such as, for example, water-soluble zinc salts; phosphates; polyphosphates; phosphonic acid and their salts, for example, acetodiphosphonic acid, nitrilo trismethylene phosphonic acid and methylamino dimethylene phosphonocarboxylic acids and their salts, for example, those described in German Offenlegungsschrift No. 2,632,774, hydroxyphosphonoacetic acid, 2-phosphonobutane-1,2,4-tricarboxylic acid and those disclosed in GB Pat. No. 1,572,406; nitrates, for example sodium nitrate; nitrites e.g. sodium nitrite; molybdates e.g. sodium molybdate; tungstates; silicates e.g. sodium silicate; benzotriazole, bis-benzotriazole or copper deactivating benzotriazole or tolutriazole derivatives or their Mannich base derivatives; N-acyl sarcosines; N-acylimino diacetic acids; ethanolamines; fatty amines; and polycarboxylic acids, for example, polymaleic acid and polyacrylic acid, as well as their respective alkali metal salts, copolymers of maleic anhydride, e.g. copolymers of maleic anhydride and sulfonated styrene, copolymers of acrylic acid e.g. copolymers of acrylic acid and hydroxyalkylated acrylic acid, and substituted derivatives of polymaleic and polyacrylic acids and their copolymers. Moreover, in such completely aqueous systems, the inhibitor used according to the invention may be used in conjunction with dispersing and/or threshold agents e.g. polymerised acrylic or methacrylic acid (or its salts) or polyacrylamide and copolymers thereof.

Further additives may be precipitating agents such as alkali metal orthophosphates, carbonates; oxygen scavengers such as alkali metal sulphites and hydrazines; sequestering agents such as nitrilotriacetic acid and its salts; antifoaming agents such as silicones e.g. polydimethylsiloxanes, distearylsebacamide, distearyl adipamide and related products derived from ethylene oxide and/or propylene oxide condensations, in addition to fatty alcohols, such as capryl alcohols and their ethylene oxide condensates; and biocides e.g. amines, quaternary ammonium compounds, chlorophenols, sulphur-containing compounds such as sulphones, methylene bis thiocyanates and carbamates, isothiazolones, brominated propionamides, triazines, phosphonium compounds, chlorine and chlorine-release agents and organometallic compounds such as tributyl tin oxide may be used.

If the aqueous applicational medium, component (b), is not completely aqueous e.g. an aqueous machining fluid formulation, it may be e.g. a water dilutable cutting or grinding fluid.

The aqueous machining fluid formulations treated according to the invention may be e.g. metal working formulations. By "metal working" we mean reaming, broaching, drawing, spinning, cutting, grinding, boring, milling, turning, sawing, non-cutting shaping, rolling or quenching. Examples of water-dilutable cutting or grinding fluids into which the corrosion inhibiting compound may be incorporated include:

(a) Aqueous concentrates of one or more corrosion inhibitors, and optionally one or more anti-wear additives, used at dilutions of 1:50 or 1:100, which are usually employed as grinding fluids;

(b) Polyglycols containing biocides, corrosion inhibitors and anti-wear additives which are used at dilutions of 1:20 to 1:40 for cutting operations and 1:60 to 1:80 for grinding;

(c) Semi-synthetic cutting fluids similar to (b) but containing in addition 10 to 25% oil with sufficient emulsifier to render the water diluted product translucent;

(d) An emulsifiable mineral oil concentrate containing, for example, emulsifiers, corrosion inhibitors, extreme pressure/anti-wear additives, biocides, antifoaming agents, coupling agents etc; they are generally diluted from 1–10 to 1:50 with water to a white opaque emulsion;

(e) a product similar to (d) containing less oil and more emulsifier which on dilution to the range 1:50 to 1:100 gives a translucent emulsion for cutting or grinding operations.

For those partly-aqueous systems in which the aqueous applicational medium is an aqueous machining fluid formulation the inhibitor component (B) may be used singly, or in admixture with other additives e.g. known further corrosion inhibitors or extreme-pressure additives.

Examples of other corrosion inhibitors which may be used in these aqueous systems, in addition to the inhibitor component (b) used according to the invention, include the following groups:

(a) organic acids, their esters or ammonium, amine alkanolamine and metal salts, for example, benzoic acid, p-tert-butyl benzoic acid, disodium sebacate, triethanolamine laurate, iso-nonanoic acid, triethanolamine salts of p-toluene sulphonamido caproic acid, triethanolamine salt of benzene sulphonamido caproic acid, triethanolamine salts of 5-ketocarboxylic acid derivatives as described in European Pat. No. 41927, sodium N-lauroyl sarcosinate or nonylphenoxy acetic acid;

(b) Nitrogen containing materials such as the following types: fatty acid alkanolamides; imidazolines, for example, 1-hydroxyethyl-2-oleyl-imidazolines; oxazolines; triazoles for example, benzotriazoles; or their Mannich base derivatives; triethanolamines; fatty amines; inorganic salts, for example, sodium nitrate; and the carboxy-triazine compounds described in European Patent Application No. 46139.

(c) Phosphorus containing materials such as the following types: amine phosphates, phosphonic acids or inorganic salts, for example, sodium dihydrogen phosphate or zinc phosphate;

(d) Suphur containing compounds such as the following types: sodium, calcium or barium petroleum sulphonates, or heterocyclics, for example, sodium mercaptobenzothiazole.

Nitrogen containing materials, particularly triethanolamine, are preferred.

Examples of extreme pressure additives which may be present in the systems according to the present invention include sulphur and/or phosphorus and/or halogen containing materials, for instance, sulphurised sperm oil, sulphurised fats, tritolyl phosphate, chlorinated paraffins or ethoxylated phosphate esters.

The following Examples further illustrate the present invention. Parts and percentages shown therein are by weight unless otherwise stated, the temperatures are indicated in °C.

EXAMPLE 1

1-(Benzothiazol-2-ylthio)-propane-2,3-dicarboxylic acid mono(dodecylamide)

A mixture of 6.5 parts of 3-(benzothiazol-2-ylthio)-propane-1,2-dicarboxylic anhydride and 4.3 parts of dodecylamine is heated at 55° during 3 hours to give a mixture of the two isomeric mono-dodecylamides as a yellow oil.

'H NMR ($\delta$CDCl$_3$/DMSO): 0.85 (m, 3H); 1.22 (s, 20H); 2.63 (m, 2H); 3.14 (m, 3H); 3.58 (m, 2H); 7.17 (m, 2H); 7.56 (m, 2H).

EXAMPLE 2

1-(Benzothiazol-2-ylthio)-propane-2,3-dicarboxylic acid mono(butylamide)

A solution of 7 parts of 3-(benzothiazol-2-ylthio)-propane-1,2-dicarboxylic anhydride and 1.8 parts of n-butylamine in 50 parts of diethylether is heated at 35° for 4 hours. Evaporation of the solution gives a mixture of the two isomeric N-butyl-monoamides as a viscous oil.

'H NMR ($\delta$CDCl$_3$): 0.82 (t, 3H); 1.18 (m, 4H); 2.70 (m, 2H); 3.16 (m, 3H); 3.50 (m, 2H); 7.10 (m, 2H); 7.58 (m, 2H).

A mixture of 7 parts of 3-(benzothiazol-2-ylthio)-propane-1,2-dicarboxylic anhydride and 3.6 parts of n-butylamine is heated at 55° for 3 hours to give the butylammonium salt of the above amide as a viscous oil (mixture of isomers).

'H NMR ($\delta$CDCl$_3$): 0.85 (m, 6H); 1.32 (m, 8H); 2.65 (m, 2H); 3.10 (m, 5H); 3.48 (m, 2H); 6.75 (t, 1H); 7.15 (m, 2H); 7.55 (m, 2H).

EXAMPLE 3

N-Octyl-3-(benzothiazol-2-ylthio)-propane-1,2-dicarboxylic acid imide

A solution of 7 parts of 3-(benzothiazol-2-ylthio)-propane-1,2-dicarboxylic anhydride and 3.2 parts of n-octylamine in 100 parts of toluene is heated at 112° for 5 hours until no more water is evolved. Evaporation of the solution gives N-octyl(benzothiazol-2-ylthio)-propane-1,2-dicarboxylic acid imide as a brown oil.

'H NMR ($\delta$CDCl$_3$): 0.85 (m, 3H); 1.25 (m, 12H); 2.78 (d, 2H); 3.42 (m, 4H); 3.90 (m, 1H); 7.12 (m, 2H); 7.60 (m, 2H).

EXAMPLE 4

1-(Benzothiazol-2-ylthio)-propane-2,3-dicarboxylic acid monoanilide

A solution of 7 parts of 3-(benzothiazol-2-ylthio)-propane-1,2-dicarboxylic anhydride and 2.3 parts of aniline in 50 parts of diethylether is heated at 35° for 5 hours. Filtration of the resulting mixture and evaporation of the solution gives a mixture of the isomerics monoanilides, melting at 136°–9°.

'H NMR ($\delta$-DMSO): 2.65 (m, 2H); 3.22 (m, 1H); 3.58 (m, 2H); 7.12 (m, 2H); 7.60 (m, 2H).

EXAMPLE 5

Benzothiazol-2-ylthiosuccinic acid monobutylamide

A mixture of 6.6 parts of (benzothiazol-2-ylthio)succinic anhydride, 1.8 parts of n-butylamine and 50 parts of diethylether is heated at 35° C. for 3 hours. Filtration and evaporation of the resulting solution gives a mixture of the two isomeric N-butyl-monoamides, melting at 115°14 120°.

'H NMR (δ-CDCl$_3$/DMSO): 0.85 (t, 3H); 1.35 (m, 4H); 3.14 (m, 4H); 4.90 (m, 1H); 7.35 (m, 2H); 7.81 (m, 2H).

A mixture of 6.6 parts of (benzothiazol-2-ylthio)succinic anhydride and 3.7 parts of n-butylamine is heated at 55° for 5 hours to give the butylammonium salt of the above monoamide mixture, melting at 97°–105°.

'H NMR (δ-CDCl$_3$2): 0.82 (t, 6H); 1.35 (m, 8H); 3.14 (m, 6H); 4.80 (m, 1H); 6.83 (t, 1H); 7.22 (m, 2H); 7.65 (m, 2H).

EXAMPLE 6

(Benzothiazol-2-ylthio)-succinic acid mono(dodecylamide)

A mixture of 7 parts of (benzothiazol-2-ylthio)succinic anhydride, 4.8 parts of dodecylamine and 60 parts of diethyl ether is heated at 35° for 3 hours. Filtration of the resulting mixture gives a mixture of the two isomeric mono(dodecylamides), melting at 117°–121°.

'H NMR (δCDCl$_3$/DMSO): 0.85 (m, 3H); 1.22 (m, 20-H); 3.15 (m, 4H); 4.84 (m, 1H); 7.25 (m, 2H); 7.42 (m, 2H).

EXAMPLE 7

(Benzothiazol-2-ylthio)-succinic acid monoanilide

A mixture of 6.6 parts of (benzothiazol-2-ylthio)succinic anhydride, 2.3 parts of aniline and 50 parts of diethylether is heated at 35° for 3 hours. Filtration of the resulting mixture gives a mixture of the two isomeric monoanilides, melting at 165°–8°.

'H NMR (δCDCl$_3$/DMSO): 3.2 (m, 2H); 4.85 (m, 1H); 7.05 (m, 2H); 7.84 (m, 7H).

EXAMPLE 8

N-Octyl 1-(benzothiazol-2-ylthio)succinimide

A solution of 6.4 parts of (benzothiazol-2-ylthio)succinic anhydride and 3.1 parts of n-octylamine in 100 parts of toluene is heated at 112° C. for 7 hours. Evaporation of the solution gives N-octyl 1-(benzothiazol-2-ylthio)succinimide as brown oil.

+H NMR (δCDCl$_3$): 0.85 (m, 3H); 1.22 (m, 12H); 3.18 (d, 2H); 3.55 (t, 2H); 4.30 (t, 1H); 7.12 (m, 2H); 7.54 (m, 2H).

EXAMPLE 9

N,N'-Dicyclohexyl-3-benzothiazol-2-ylthio)-1,2-propane dicarboxylic acid diamide 150 parts of absolute ethanol are saturated with dry hydrogen chloride gas at room temperature. 50 parts of 3-(benzothiazol-2-ylthio)-propane-1,2-dicarboxylic acid are then added and the mixture heated to reflux. The resulting solution is then stirred at reflux for 3 hours. Excess ethanol is removed by heating at 90° under vacuum of 0.1 mm to give diethyl 3-(benzothiazol-2-ylthio)-propane-1,2-dicarboxylate as a yellow liquid.

'H NMR (δCDCl$_3$): 1.4 (t, 6H); 3.0 (d, 2H); 3.5 (m, 1H); 3.8 (m, 2H); 4.2 (m, 4H); 7.2 (m, 2H); 7.7 (m, 2H).

18.5 parts of diethyl 3-(benzothiazol-2-ylthio)-propane- 1,2-dicarboxylate are stirred with 31.1 parts cyclohexylamine for 12 hours at 95° C. The mixture is cooled and toluene added with stirring. The resulting solid is filtered off, washed with toluene and dried to give N,N'-dicyclohexyl 3-(benzothiazol-2-ylthio)-1,2-propane dicarboxylic acid diamide, melting at 147°–49° C.

'H NMR (δDMSOD$_6$): 1.6 (m, 20H); 2.5 (d, 2H); 3.2 (d, 1H); 3.6 (m, 4H); 7.3 (m, 2H); 7.8 (m, 2H).

EXAMPLE 10

N,N'-Dibutyl 3-(benzothiazol-2-ylthio)-propane-1,2-dicarboxylic acid diamide 18.0 parts of diethyl 3-(benzothiazol-2-ylthio)-propane-1,2-dicarboxylate and 30.0 parts of n-butylamine are stirred for 3 hours at 90° C. Volatile material are removed by heating at 90° C. under a vacuum of 0.1 mm to give N,N'-dibutyl 3-(benzothiazol-2-ylthio)-1,2-propane dicarboxylic acid diamide as a viscous liquid.

'H NMR (δCDCl$_3$): 1.1 (t, 6H); 1.5 (m, 8H); 2.8 (m, 2H); 3.3 (m, 5H); 3.7 (m, 2H); 7.2 (m, 2H); 7.5 (m, 2H).

EXAMPLE 11

2-(Benzothiazol-2-ylthio)-propionic acid amide

A finely powdered mixture of 16.8 g of 2-mercaptobenzothiazole and 7.5 g of acrylic amide is added at 45°–50° in the course of 1 hour to 100 ml 70% sulfuric acid, with stirring. After a further hour at 45°–50°, the rection mixture is poured into ice water. The precipitate is filtered off, washed with water and dried. The obtained 2-(benzthiazol-2-ylthio)-propionic acid amide is recrystallized from ethylacetate and melts at 144°–145°.

Analysis (C$_{10}$H$_{10}$N$_2$OS$_2$): calculated: 50.40%C; 4.23%H; 11.76%N; 26.91%S. found: 50.2%C; 4.3 H; 11.6%H; 26.6%S.

EXAMPLE 12

Anticorrosive Paint

An alkyld resin paint is prepared using the following formulation:

- 40 parts of Alphthalat ® AM380 (60% solution in xylene), alkyd resin made by Reichhold Albert Chemie AG,
- 4 parts of iron oxide red 225 made by Bayer AG,
- 17.4 parts of talc (micronised),
- 13 parts of micronised calcium carbonate (Millicarb ®, Plüss-Staufer AG),
- 0.3 part of skin prevention agent Luaktin ® (BASF),
- 0.6 part of 8% cobalt naphthenate solution and
- 24.7 parts of 6:40 xylene/ethylglycol mixture.

The corrosion inhibitors indicated in the table which follow are previously dissolved in part of the solvent and are added to the paint. The paint is ground with glass beads for 7 days until a pigment and extender particle size of 15 μm is achieved.

The paint is sprayed on to sand-blasted steel sheets measuring 7×13 cm in a layer thickness of approximately 50 μm after drying. After drying at room temperature for 7 days, the samples are cured for 60 minutes at 60° C.

Two cross-shaped cuts 4 cm long are cut into the cured paint surface, until the metal is reached, using a Bonder cross-cut device. An edge protection agent (Icosit ® 255) is applied to the edges in order to protect them.

The samples are now subjected to a salt spray test as specified in ASTM B 117 for a duration of 600 hours. The condition of the coating is assessed after every 200 hours of weathering, specifically the degree of bubbling (as specified in DIN 53,209) at the cross-cut and on the painted surface and also the degree of rusting (as specified in DIN 53,210) on the entire surface.

At the end of the test, the coating is removed by treatment with concentrated sodium hydroxide solution, and the corrosion of the metal at the cross-cut (as specified in DIN 53,167) and also over the remainder of the surface is assessed. In every case the assessment is made on the basis of a 6-stage scale. The corrosion protection value CP is given by the sum of the assessment of the coating and the assessment of the metal surface. The higher this value, the more effective the inhibitor under test.

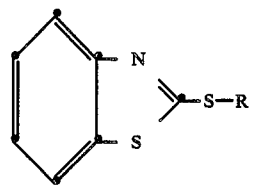

I

| Ex. | R | Amount added | Assessment of coating | Assessment of metal | CP |
|---|---|---|---|---|---|
| 1 | —CH$_2$—CH(COOH)—CH$_2$CONHC$_{12}$H$_{25}$ | 2% | 4.5 | 4.6 | 9.1 |
|   | + |  |  |  |  |
|   | —CH$_2$—CH(CONHC$_{12}$H$_{25}$)—CH$_2$COOH | 4% | 4.0 | 3.3 | 7.3 |
| 2 | —CH$_2$—CH(COOH)—CH$_2$CONHC$_4$H$_9$ | 2% | 4.7 | 5.0 | 9.7 |
|   | + |  |  |  |  |
|   | —CH$_2$—CH(CONHC$_4$H$_9$)—CH$_2$COOH | 4% | 4.7 | 4.7 | 9.4 |
| 4 | —CH$_2$—CH(COOH)—CH$_2$—CONHphenyl | 2% | 3.4 | 1.5 | 4.9 |
|   | + |  |  |  |  |
|   | —CH$_2$—CH(CONHphenyl)—CH$_2$—COOH | 4% | 3.0 | 1.7 | 4.7 |
| 5 | —CH(COOH)—CH$_2$CONHC$_4$H$_9$ | 2% | 2.8 | 1.5 | 4.3 |
|   | + |  |  |  |  |
|   | —CH(CONHC$_4$H$_9$)—CH$_2$COOH | 4% | 2.6 | 0.6 | 3.2 |
| 6 | —CH(COOH)—CH$_2$CONHC$_{12}$H$_{25}$ | 2% | 3.6 | 3.8 | 7.4 |
|   | + |  |  |  |  |
|   | —CH(CONHC$_{12}$H$_{25}$)—CH$_2$COOH | 4% | 1.6 | 0.6 | 2.2 |
| 7 | —CH(COOH)—CH$_2$CONHphenyl | 2% | 4.5 | 5.0 | 9.5 |
|   | + |  |  |  |  |
|   | —CH(CONHphenyl)—CH$_2$COOH | 4% | 2.5 | 0.6 | 3.1 |
| 8 | succinimide derivative with N—C$_8$H$_{17}$ (—CH—C(=O)—N(C$_8$H$_{17}$)—C(=O)—CH$_2$—) | 2% | 4.4 | 3.8 | 8.2 |
|   |  | 4% | 4.7 | 4.3 | 9.0 |
| 3 | —CH$_2$—CH— with N—C$_8$H$_{17}$ succinimide ring | 2% | 3.7 | 3.8 | 7.5 |
|   |  | 4% | 2.9 | 1.5 | 4.4 |
| 9 | —CH$_2$—CH(CONHcyclohexyl)—CH$_2$CONHcyclohexyl | 2% | 4.1 | 4.0 | 8.1 |
|   |  | 4% | 3.8 | 3.3 | 7.1 |

-continued

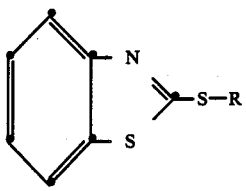
I

| Ex. | R | Amount added | Assessment of coating | Assessment of metal | CP |
|---|---|---|---|---|---|
| 10 | —CH₂—CH—CH₂CONHC₄H₉<br>          \|<br>          CONHC₄H₉ | 2%<br>4% | 4.9<br>4.5 | 3.5<br>1.7 | 8.4<br>6.2 |
| 11 | —CH₂—CH₂CONH₂ | 2%<br>4% | 4.3<br>3.4 | 4.8<br>3.9 | 9.1<br>7.3 |
| 12 | —CH₂CONHCH₂CH₂OH | 2%<br>4% | 3.7<br>2.2 | 3.3<br>1.0 | 7.0<br>3.2 |
| 13 | Control | — | 1.6 | 0.8 | 2.4 |

What is claimed is:

1. A composition which comprises
(A) (a) an aqueous or non-aqueous coating composition suitable for preparing a surface coating which is a paint, or
(b) a wholly or partly aqueous non-coating system which is a cooling water system, an air-conditioning system, a steam-generating system, a seawater evaporator, a hydrostatic cooker, a closed circuit heating or refrigerant system, an aqueous scouring or metal-working formulation, an antifreeze composition or a water-based hydraulic fluid composition, and
(B) an effective corrosion-inhibiting amount of a compound of formula II

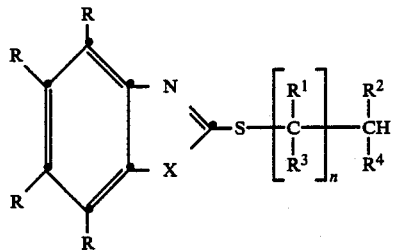
II in which
X is sulfur;
R is each independently of one another hydrogen, alkyl, haloalkyl, alkoxy, alkylthio, alkylsulfonyl, cycloalkyl, phenyl, alkylphenyl, phenylalkyl, halogen, cyano, nitro, hydroxy, —COOH, —COOalkyl or a primary-, secondary- or tertiary-amino or carbamoyl group;
n is 0 or 1;
$R^1$, $R^2$, $R^3$ and $R^4$ are independently hydrogen, alkyl, hydroxyalkyl, haloalkyl, cyanoalkyl, alkoxyalkyl, phenyl, phenylalkyl, said phenyl or said phenylalkyl substituted by one or two of halogen, of nitro, of alkyl, of alkoxy, of carboxy or of hydroxy; cyano, carboxy, alkyl substituted by carboxy or by —CONZ₁Z₂; or —CONZ₁Z₂ where
Z₁ and Z₂ are independently hydrogen, C₁–C₁₈-alkyl, said alkyl interrupted by one or more O or S atoms or by one or more NRᵒ groups where Rᵒ is C₁–C₁₈-alkyl, C₃–C₁₂-cycloalkyl, phenyl, naphthyl, C₇–C₉-phenylalkyl or C₇–C₁₈-alkylphenyl; or said alkyl substituted by —SH, by —NH₂, by —COOH, by —COORᵒ, by —CONH₂, by —CN or by halogen; C₂–C₁₀-hydroxyalkyl or said hydroxyalkyl interrupted by one or more NRᵒ groups or by one or more oxygen atoms; C₃–C₁₈-alkenyl, C₃–C₁₂-cycloalkyl or said cycloalkyl substituted by C₁–C₄-alkyl, by —OH, by —SH, by —COOH, by —COORᵒ, by —CONH₂, by —CN or by halogen;
C₇–C₉-phenylalkyl, C₇–C₁₈-alkylphenyl, or C₆–C₁₀-aryl or said phenyl or said aryl substituted by C₁–C₁₂-alkoxy, by C₁–C₁₂-alkylthio, by halogen or by nitro; or
Z₁ and Z₂ together form a straight or branched alkylene of 3 to 7 carbon atoms or said alkylene interrupted by O, by S or by NRᵒ; or
(B) is a compound of formula II where the moiety

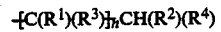

contains a group of formula III or IIIa

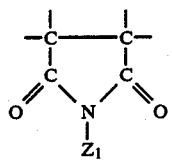
III

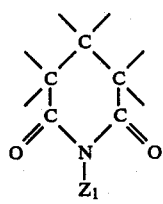
IIIa or where $R^1$ and $R^2$ or $R^1$ and $R^3$ together form a straight or branched alkylene, or said alkylene substituted by one or two —COOH or by one or two —CONZ₁Z₂; or where $R^1$ and $R^2$ form a direct bond;

with the proviso that at least two of $R^1$, $R^2$, $R^3$ and $R^4$ must contain a carboxy group or a derivative thereof which is a —$CONZ_1Z_2$ group, —CN or an imide of formula III or IIIa with the further proviso that at least one of —$CONZ_1Z_2$, —CN or imide groups must be present, or (B) is a non-toxic base addition salt of a compound of formula II which contains a free carboxy group.

2. A composition according to claim 1 where in the compound of formula II $R^1$, $R^2$, $R^3$ and $R^4$ are independently hydrogen, $C_1$-$C_4$-alkyl, —CN, —COOH, —$CONZ_1Z_2$ or said alkyl substituted by —CN, by —COOH or by —$CONZ_1Z_2$.

3. A composition according to claim 1 where in the compound of formula II $R^4$ is —COOH, —$CONZ_1Z_2$ or $C_1$-$C_4$-alkyl substituted by —COOH or by —$CONZ_1Z_2$.

4. A composition according to claim 1 where in the compound of formula II at least two of $R^1$, $R^2$, $R^3$ and $R^4$ are —COOH, —$CONZ_1Z_2$ or alkyl substituted by —COOH or by —$CONZ_1Z_2$.

5. A composition according to claim 1 where in the compound of formula II two groups —$CONZ_1Z_2$ or one —$CONZ_1Z_2$ and one —COOH are present on adjacent carbon atoms.

6. A composition according to claim 1 where in the compound of formula II $Z_1$ and $Z_2$ are independently hydrogen, $C_1$-$C_{12}$ alkyl, $C_2$-$C_4$ hydroxyalkyl, $C_3$-$C_{12}$-alkoxyalkyl, cyclohexyl, benzyl, phenyl, tolyl or naphthyl or $Z_1$ and $Z_2$ together are tetramethylene, pentamethylene or 3-oxapentamethylene.

7. Composition according to claim 1 which contains as component (B), an amide containing compound of formula II in which X is sulphur.

8. Composition according to claim 7 which contains as component (B), a half-amide containing compound of formula II in which X is sulphur.

9. Composition according to claim 1 wherein, in the compound of formula II one of the substituents R is hydrogen, $C_1$-$C_4$ alkoxy or amino and the other three groups R are each hydrogen.

10. Composition according to claim 9 wherein all four groups R are simultaneously hydrogen.

11. Composition according to claim 1 which contains as component (A) an aqueous or non-aqueous coating composition.

12. Composition according to claim 11 wherein the non-aqueous coating composition contains, as film-former, an epoxide resin, polyurethane resin, aminoplast resin, acrylic resin, polyester resin, alkyd resin or a mixture of such resins, polyvinylbutyral, polyvinylacetate, polyvinyl chloride or their polymers, a phenol resin, a chlorinated rubber, a styrene-butadiene copolymer, a drying oil or a cellulose ester.

13. Composition according to claim 11 wherein the aqueous coating composition contains, as film-former, an alkyd, polyester, acrylic, polyurethane, epoxide, phenoplast condensate or aminoplast precondensate resin, or mixture of these resins, or a homo- or co-polymer of vinyl ethers, vinyl esters, styrene, vinylidene chloride or vinyl chloride.

14. Composition according to claim 11 which also contains a pigment, dyestuff, filler or other customary additive for coatings.

15. Composition according to claim 11 which contains a basic filler or basic pigment.

16. Composition according to claim 11 containing, apart from component (B), one or more further corrosion inhibitors which are organic, metallorganic or inorganic compounds.

17. Composition according to claim 11 containing 0.1 to 20 weight % of component (B), based on the solids content of the coating composition.

18. Composition according to claim 17 containing 0.5 to 5 weight % of component (B), based on the solids content of the coating composition.

19. Composition according to claim 1 wherein (A) is an aqueous non-coating medium which contains 0.1 ppm to 5 weight % of component (B), based on the total weight of the aqueous non-coating system.

20. Composition according to claim 1 wherein (A) is a non-coating system which is wholly aqueous and contains, in addition to component (B), one or more other corrosion inhibitors, dispersing agents, precipitation agents, oxygen scavengers, complexing agents, antifoam agents or biocides.

21. Composition according to claim 1 wherein (A) is a non-coating system which is an aqueous metal working formulation containing, in addition to component (B), a further corrosion inhibitor or an extreme pressure additive.

22. A compound of formula II

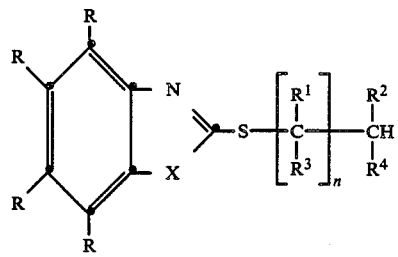

in which

X is sulphur;

R is each independently of one another hydrogen, alkyl, haloalkyl, alkoxy, alkylthio, alkylsulfonyl, cycloalkyl, phenyl, alkylphenyl, phenylalkyl, halogen, cyano, nitro, hydroxy, —COOH, —COOalkyl or a primary-, secondary- or tertiary-amino or carbamoyl group;

n is 0 or 1;

$R^1$, $R^2$, $R^3$ and $R^4$ are independently hydrogen, alkyl, hydroxyalkyl, haloalkyl, cyanoalkyl, alkoxyalkyl, phenyl, phenylalkyl, said phenyl or said phenylalkyl substituted by one or two of halogen, of nitro, of alkyl, of alkoxy, of carboxy or of hydroxy; cyano, carboxy, alkyl substituted by carboxy or by —$CONZ_1Z_2$; or —$CONZ_1Z_2$ where $Z_1$ and $Z_2$ are independently hydrogen, $C_1$-$C_{18}$-alkyl, said alkyl interrupted by one or more O or S atoms or by one or more $NR^o$ groups where $R^o$ is $C_1$-$C_{18}$-alkyl, $C_3$-$C_{12}$-cycloalkyl, phenyl naphthyl, $C_7$-$C_9$-phenylalkyl or $C_7$-$C_{18}$-alkylphenyl; or said alkyl substituted by —SH, by —$NH_2$, by —COOH, by —$COOR^o$, by —$CONH_2$, by —CN or by halogen; $C_2$-$C_{10}$-hydroxyalkyl or said hydroxyalkyl interrupted by one or more $NR^o$ groups or by one or more oxygen atoms; $C_3$-$C_{18}$-alkenyl, $C_3$-$C_{12}$-cycloalkyl or said cycloalkyl substituted by $C_1$-$C_4$-alkyl, by —OH, by —SH, by —COOH, by —$COOR^o$, by —$CONH_2$, by —CN or by halogen; $C_7$-$C_9$-phenylalkyl, $C_7$-$C_{18}$-alkylphenyl, or $C_6$-$C_{10}$-aryl or said phenyl or said aryl substituted by $C_1$-$C_{12}$-alkoxy, by $C_1$-$C_{12}$-alkylthio, by halogen or by nitro; or $Z_1$ and $Z_2$ together form a straight or branched alkylene of 3 to 7 carbon atoms or said alkylene interrupted by O, by S or by $NR^o$; or is a compound of formula II where the moiety

contains a group of formula III or IIIa

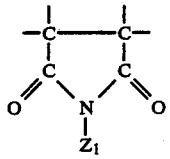   III

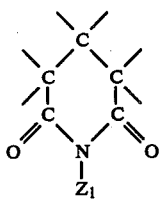   IIIa or where $R^1$ and $R^2$ or $R^1$ and $R^3$ together form a straight or branched alkylene, or said alkylene substituted by one or two —COOH or by one or two —$CONZ_1Z_2$; or where $R^1$ and $R^2$ form a direct bond;

with the proviso that at least two of $R^1$, $R^2$, $R^3$ and $R^4$ must contain a carboxy group or a derivative thereof which is a —$CONZ_1Z_2$ group, —CN or an imide of formula III or IIIa with the further proviso that at least one of —$CONZ_1Z_2$, —CN or imide groups must be present.

23. A compound according to claim 22 wherein the moiety

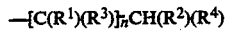

contains 2, 3 or 4 groups of the formula —$CONZ_1Z_2$.

24. A compound according to claim 22 wherein the moiety

contains at least one group —$CONZ_1Z_2$ and at least one group —COOH.

25. A compound according to claim 22 wherein n is 1, $R^1$ and $R^3$ are hydrogen, $R^2$ and $R^4$ are hydrogen, $C_1$-$C_4$-alkyl, —CN, —COOH, —$CONZ_1Z_2$ or alkyl substituted by —CN, —COOH or —$CONZ_1Z_2$ wherein the moiety

contains a group of formula III or IIIa

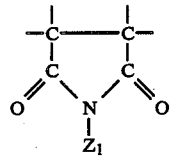   III

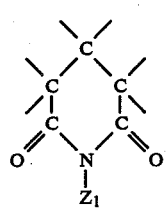   IIIa

26. A compound according to claim 22 wherein the moiety

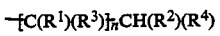

contains 2, 3 or 4 —CN groups.

* * * * *